(12) United States Patent
Koike et al.

(10) Patent No.: US 10,352,226 B2
(45) Date of Patent: Jul. 16, 2019

(54) PARTICULATE MATTER DETECTION ELEMENT

(71) Applicant: DENSO CORPORATION, Kariya, Aichi-pref. (JP)

(72) Inventors: Kazuhiko Koike, Nishio (JP); Hironobu Shimokawa, Nishio (JP); Masayuki Tamura, Kariya (JP)

(73) Assignee: DENSO CORPORATION, Kariya (JP)

( * ) Notice: Subject to any disclaimer, the term of this patent is extended or adjusted under 35 U.S.C. 154(b) by 202 days.

(21) Appl. No.: 15/538,796

(22) PCT Filed: Dec. 21, 2015

(86) PCT No.: PCT/JP2015/085679
§ 371 (c)(1),
(2) Date: Jun. 22, 2017

(87) PCT Pub. No.: WO2016/104428
PCT Pub. Date: Jun. 30, 2016

(65) Prior Publication Data
US 2017/0350300 A1    Dec. 7, 2017

(30) Foreign Application Priority Data
Dec. 23, 2014    (JP) .................................. 2014-259592

(51) Int. Cl.
*G01M 15/10*    (2006.01)
*F01N 11/00*    (2006.01)
(Continued)

(52) U.S. Cl.
CPC .............. *F01N 11/007* (2013.01); *F01N 3/00* (2013.01); *F01N 3/023* (2013.01); *F01N 13/008* (2013.01);
(Continued)

(58) Field of Classification Search
USPC ...................................................... 73/114.71
See application file for complete search history.

(56) References Cited

U.S. PATENT DOCUMENTS

2010/0206167 A1* 8/2010 Okayama ........... G01N 15/0656
96/19
2012/0103059 A1* 5/2012 Kimata ................... F01N 11/00
73/23.33
(Continued)

FOREIGN PATENT DOCUMENTS

JP            6-242043       9/1994
JP            2012-78130     4/2012

*Primary Examiner* — Eric S. McCall
(74) *Attorney, Agent, or Firm* — Nixon & Vanderhye PC

(57) ABSTRACT

A particulate matter sensor detecting particulate matter in exhaust emissions is provided, which is resistant to having sensor surfaces buried by particulate matter residue. Detection electrodes are provided, with alternating polarity, laminated in a laminating direction, separated by insulation. Of the detection electrodes, first detection electrodes of one polarity and second detection electrodes of the other polarity are exposed perpendicular to the laminating direction. In the direction perpendicular to the laminating direction, the particulate matter sensor has target accumulating parts on which the particulate matter is accumulated. In the target accumulating parts, the thickness W1 of the first detection electrodes in the laminating direction is greater than the thickness W2 of the second detection electrodes in the laminating direction.

2 Claims, 3 Drawing Sheets

(51) Int. Cl.
  *F01N 3/00* (2006.01)
  *F01N 3/023* (2006.01)
  *G01N 27/04* (2006.01)
  *F01N 13/00* (2010.01)
  *G01N 15/06* (2006.01)

(52) U.S. Cl.
  CPC ...... *G01M 15/102* (2013.01); *G01N 15/0656* (2013.01); *G01N 27/04* (2013.01); *F01N 2560/05* (2013.01); *F01N 2560/12* (2013.01)

(56) References Cited

U.S. PATENT DOCUMENTS

| | | | | |
|---|---|---|---|---|
| 2012/0266646 | A1* | 10/2012 | Maeda | F02D 41/1466 73/1.06 |
| 2015/0020576 | A1* | 1/2015 | Lee | G01N 15/0656 73/28.02 |
| 2016/0097752 | A1* | 4/2016 | Weber | G01K 7/16 73/1.06 |
| 2017/0131185 | A1* | 5/2017 | Koike | G01N 27/04 |
| 2017/0315042 | A1* | 11/2017 | Miyagawa | G01N 27/04 |
| 2017/0322134 | A1* | 11/2017 | Koike | G01N 15/06 |
| 2018/0266934 | A1* | 9/2018 | Mouri | G01M 15/102 |
| 2018/0266936 | A1* | 9/2018 | Yamamoto | G01N 27/045 |
| 2019/0033195 | A1* | 1/2019 | Miyagawa | G01N 15/0656 |

* cited by examiner

PARTICULATE MATTER DETECTION ELEMENT

This application is the U.S. national phase of International Application No. PCT/JP2015/085679 filed on Dec. 21, 2015 which designated the U.S. and claims the benefit of priority from earlier Japanese Patent Application No. 2014-259592 filed on Dec. 23, 2014, the entire contents of each of which are incorporated herein by reference.

TECHNICAL FIELD

This invention relates to a particulate matter detection element.

BACKGROUND ART

An exhaust purification system for trapping particulate matter (i.e. PM) contained in the exhaust gases is mounted in an exhaust pipe of an internal combustion engine. The exhaust purification system is mounted with a particulate matter detection system having a particulate matter detection sensor. The particulate matter detection sensor detects an amount of the particulate matter contained in the exhaust gases. A fault detection of the exhaust purification system is performed based on information obtained by the particulate matter detection system.

A particulate matter detection element of the particulate matter detection sensor used for the exhaust purification system is, for example, shown in patent document 1. Electrodes having mutually different polarities are disposed adjacent to each other in the particulate matter detection element shown in patent document 1. In addition, a static electric field is formed by applying a voltage between the electrodes, and the static electric field traps the charged particulate matter. In addition, a variation of electric characteristics between the electrodes occurred by accumulating the particulate matter between the electrodes is determined. Thereby, an amount of the particulate matter is detected.

In this case, when an accumulation amount of the particulate matter is increased, electric characteristics between the electrodes do not change much. Thereby, sensor sensitivity may be reduced. Therefore, regeneration processing is performed at a predetermined timing, and the PM-trapping capability is recovered. The regeneration processing is performed by combusting the particulate matter due to heating by a heater or the like.

RELATED ART

Patent Document

[Patent Document 1] Japanese Unexamined Patent Application Publication No. 2012-78130

DISCLOSURE OF THE INVENTION

However, even if the particulate matter is combusted, an inorganic content of the particulate matter remains as a residue. Therefore, when accumulating the particulate matter and the regeneration processing are repeated, the residue is gradually accumulated. In addition, when the electrode becomes buried in the residue, a detection sensitivity of the sensor may be reduced. In addition, PM detection may be unable.

The present disclosure has been made in view of such background and provides a particulate matter detection element, which is capable of reducing burying of detection electrodes by a residue of particulate matter, and capable of preventing reducing of detection sensitivity.

One embodiment of the present disclosure is the particulate matter detection element having the detection electrodes and a laminated part. The detection electrodes detect the particulate matter included in the exhaust gases discharged from an internal combustion engine. The laminated part laminates a plurality of insulating members, which are made up of materials which are an electric insulating property, and the detection electrodes. In a laminating direction of the detection electrodes and the insulating members, the adjacent detection electrodes have mutually different polarities. In a direction perpendicular to the laminating direction, at least a part of the detection electrodes is exposed from the insulating members. In addition, in the direction perpendicular to the laminating direction, there are target accumulating parts accumulating a part of the particulate matter in the particulate matter detection element. In each of the target accumulating parts, the thickness of each of the detection electrodes having a first polarity in the laminating direction is larger than the thickness of each of the detection electrodes having a second polarity in the laminating direction.

EMBODIMENT 1

Figure 1:
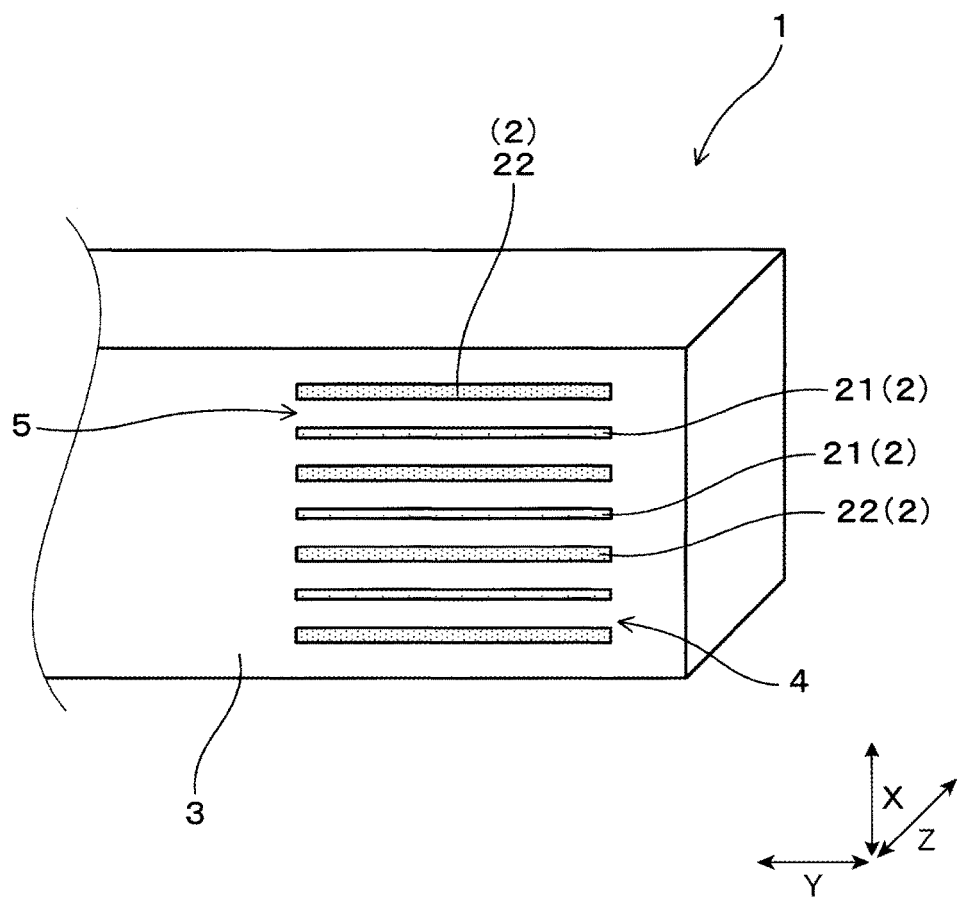
FIG. 1 shows a perspective view of a particulate matter detection element according to a first embodiment.
Figure 2:
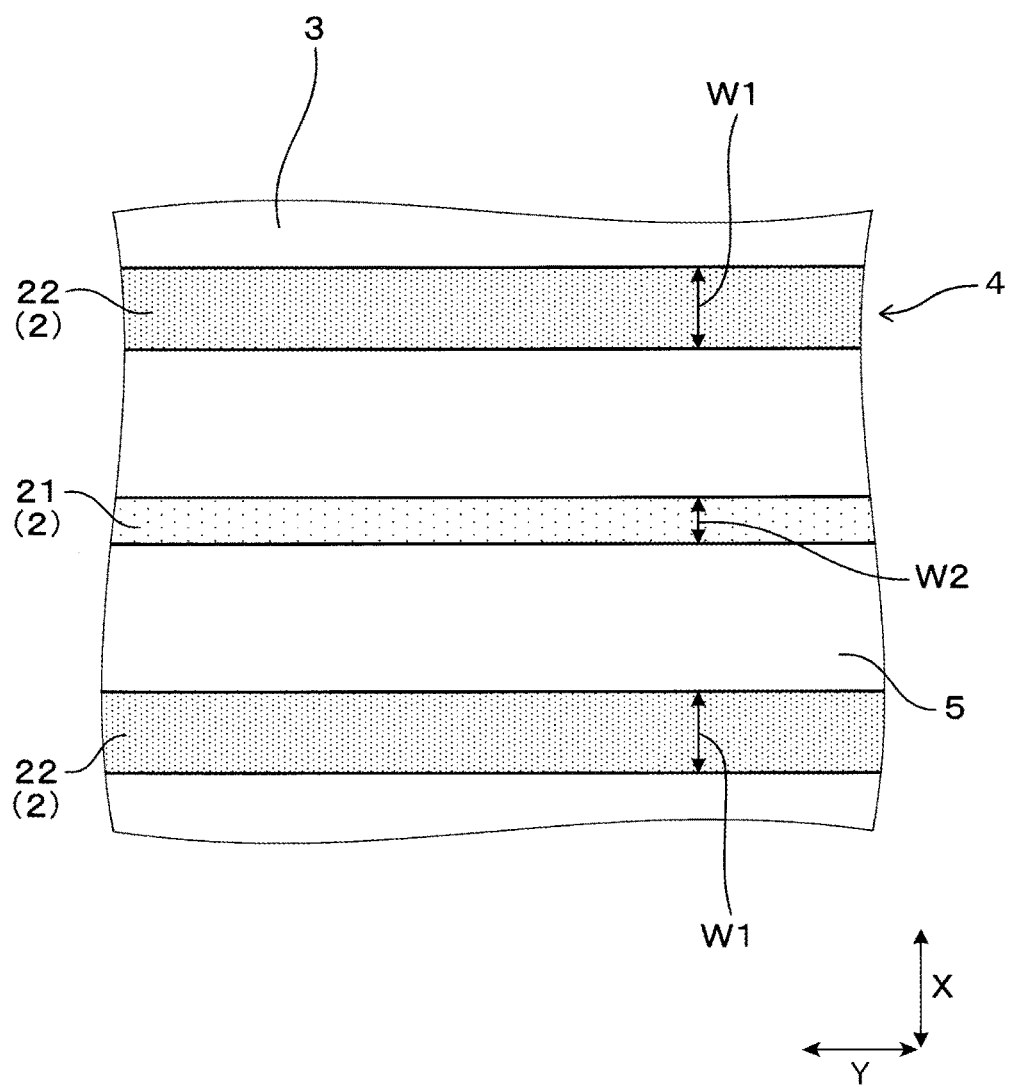
FIG. 2 shows an enlarged view of the target accumulating part of the particulate matter detection element according to the first embodiment.
Figure 3:
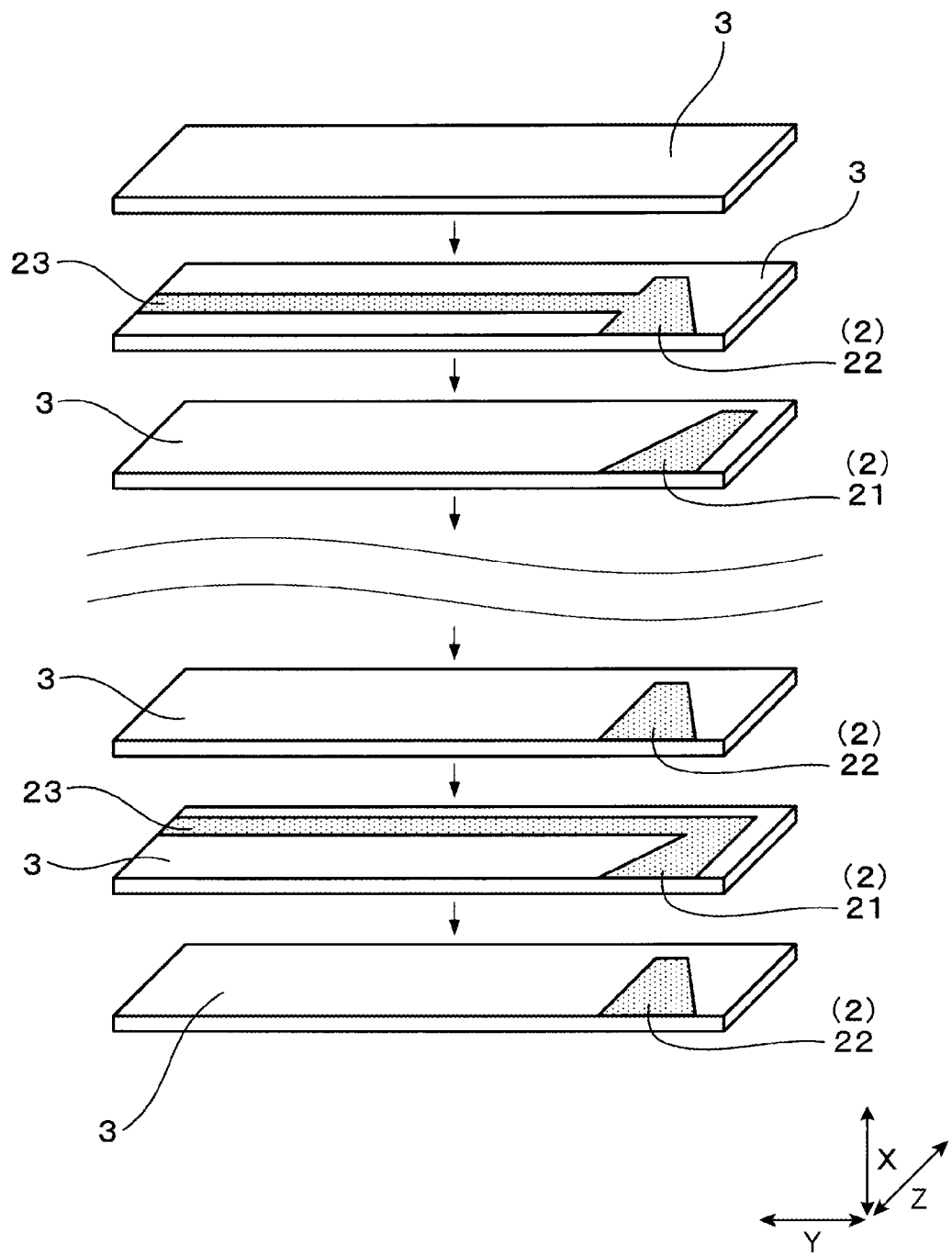
FIG. 3 shows an exploded perspective view of the particulate matter detection element according to the first embodiment.

An embodiment of a particulate matter detection element is described with FIGS. 1 to 3.

A particulate matter detection element 1 has, as shown in FIG. 1, a plurality of detection electrodes 2 and a laminated part 4. The detection electrodes 2 detect particulate matter included in the exhaust gases discharged from an internal combustion engine. The laminated part 4 is formed by laminating a plurality of insulating members 3, which are made up of electrically insulating materials, and the detection electrodes 2. In a laminating direction X of the plurality of the detection electrodes 2 and the insulating members 3, the adjacent detection electrodes 2 have mutually different polarities. In the particulate matter detection element 1, at least a part of the detection electrodes 2 is exposed from the insulating members 3 in a direction perpendicular to the laminating direction X. In addition, in the direction perpendicular to the laminating direction, there are target accumulating parts 5 accumulating a part of the particulate matter in the particulate matter detection element 1. The different polarities have a first polarity and a second polarity. As shown in FIG. 2, in each of the target accumulating parts 5, a thickness $W_1$ of each of the detection electrodes 2 having the first polarity in the laminating direction X is larger than a thickness $W_2$ of each of the detection electrodes 2 having the second polarity in the laminating direction X.

In the target accumulating part 5, the thickness $W_1$ of the detection electrode 2 having the first polarity in the laminating direction X is preferably 1.5 or more times the thickness $W_2$ of the detection electrode 2 having the second polarity in the laminating direction X.

The particulate matter detection element 1 of the present example detects the particulate matter included in the exhaust gases discharged from the internal combustion engine mounted in an automobile via an exhaust pipe. Fault detection of the exhaust purification system is performed based on information obtained by the particulate matter detection element 1.

Incidentally, in the present example, the particulate matter detection element 1 mounted in an exhaust type will be described. The main particulate matter included in the exhaust gases in the exhaust type is positively charged. That is, in the particulate matter detection element 1 of the present example, the thickness W1 of a negative electrode 22 is larger than the thickness W2 of a positive electrode 21 of the detection electrodes 2. The negative electrode 22 will be also referred to as a first detection electrode, and the positive electrode 21 will be also referred to as a second detection electrode. In addition, the thickness W1 of the negative electrode 22 is preferably 1.5 or more times the thickness W2 of the positive electrode 21.

As shown in FIG. 3, each of the insulating members 3 is made up of a plate-shaped ceramic material such as alumina, zirconia, magnesia and beryllia. The particulate matter detection element 1 has a rod shape by laminating the eight insulating members 3 in a through-thickness direction of the insulating member 3. In each of seven insulating members 3 of the eight insulating members 3, the detection electrode 2 being made up of a conductive material is formed on one end part of the insulating member 3 in a longitudinal direction of the insulating member 3 (a direction Y in figure). This one end part of the insulating member 3 is disposed on one face of the insulating member 3 in the laminating direction X. In the present embodiment, a membrane of the detection electrode 2 is formed on one of a pair of major faces of the plate-shaped insulating member 3. The laminated part 4 laminating the insulating member 3 and the detection electrode 2 alternately is formed by laminating the insulating members 3 formed with the detection electrodes 2. As shown in FIG. 1, in the laminated part 4, the positive electrode 21 of the detection electrode 2 and the negative electrode 22 of the detection electrode 2 are laminated alternately. Incidentally, in FIG. 3, a diagram that shows a thickness of the detection electrode 2 in the laminating direction X is omitted. In addition, in particular, the number of laminations of the insulating member 3 and the detection electrode 2 is not limited.

As shown in FIG. 1, the adjacent detection electrodes 2 are mutually disposed at a predetermined interval in the laminating direction X. As shown in FIG. 3, in the detection electrode 2, extraction electrodes 23 are respectively formed on the positive electrode 21 and the negative electrode 22, which are disposed on one end of the insulating members 3 in the laminating direction X. Each of the extraction electrodes 23 extends from the detection electrode 2 in a direction Y perpendicular to the laminating direction X. In the present embodiment, the positive electrodes 21 are electrically connected with each other not shown in the diagrams. In addition, the negative electrodes 22 are electrically connected with each other not shown in the diagrams. Therefore, a voltage is applied to the positive electrode 21 and the negative electrode 22 by applying an external voltage to the extraction electrode 23. Incidentally, a method of applying the voltage and a method of connecting the electrodes are not limited. As shown in FIG. 1, the target accumulating part 5 is formed on a side face of the particulate matter detection element 1 disposed in a direction Z perpendicular to the laminating direction X. The target accumulating part 5 is exposed from the insulating member 3 in a vicinity of one end of the detection electrode 2. The target accumulating part 5 is a detection face. That is, the target accumulating part 5 includes exposed faces of the detection electrodes 2 and exposed faces of the insulating members 3. Each of the exposed faces of the detection electrodes 2 is also hereinafter referred to as the detection face of the detection electrode 2. Each of the exposed faces of the insulating members 3 is also hereinafter referred to as the detection face of the insulating member 3. The exposed faces of the detection electrodes 2 are formed mutually separated on the side face of the particulate matter detection element 1. The exposed face of the insulating member 3 is disposed between the exposed faces of the detection electrodes 2.

In the target accumulating part 5 of the particulate matter detection element 1, when a voltage is applied to the detection electrode 2, an electric field is formed around the detection electrode 2. So that, the particulate matter is attracted to the detection electrode 2. In the present example, because the main particulate matter is positively charged, therefore, the particulate matter is mainly drawn to the negative electrode 22 of the detection electrode 2.

The particulate matter attached to the detection electrode 2 is moved on the surface of the detection electrode 2, that is, the detection face of the detection electrode 2. In addition, the particulate matter is accumulated between the adjacent positive electrode 21 and the negative electrode 22, that is, the detection face of the plate-shaped insulating member 3. In addition, the positive electrode 21 and the negative electrode 22, which are exposed from the target accumulating part 5, become electrically connected each other with the particulate matter accumulating on the target accumulating part 5. An electric resistance value between the positive electrode 21 and the negative electrode 22 is reduced. Accompanying a change of the electric resistance value between the detection electrodes 2, a current amount as an electrical signal passing between the detection electrodes 2 is changed. Thereby, a current value outputted from the particulate matter detection element 1 is changed.

In short, the current value outputted from the particulate matter detection element 1 is changed in accordance with an accumulation amount of the particulate matter disposed on the target accumulating part 5. In addition, the current value outputted from the particulate matter detection element 1 has information relating to the accumulation amount of the particulate matter. The accumulation amount of the particulate matter disposed on the target accumulating part 5 may be detected using the electrical current value. In the present example, a current detected from the particulate matter detection element 1 is outputted to a control unit having a shunt resistor. The control unit outputs the voltage calculated by a product of the current value and the resistance of the shunt resistor.

Next, effects of the present example will be described.

In the target accumulating part 5 of the particulate matter detection element 1, the thickness W1 in the laminating direction X of the detection electrode 2 having the first polarity is larger than the thickness W2 in the laminating direction X of the detection electrode 2 having the second polarity. Therefore, while reducing an increase of a thickness of the particulate matter detection element 1, a residue of the particulate matter may be prevented from burying the detection electrode 2.

That is, because the particulate matter included in the exhaust gases is positively and/or negatively charged, the particulate matter is easy to intensively accumulate on either one of the positive electrode and the negative electrode. Therefore, the thickness of only the detection electrode 2 at a side where the particulate matter is easily intensively accumulated is increased. Thereby, while preventing the particulate matter detection element 1 from being enlarged in the laminating direction X, the residue of the particulate matter may be prevented from burying the detection electrode 2.

In addition, when the thickness W1 is 1.5 or more times the thickness W2, the residue of the particulate matter may be prevented from burying the detection electrode 2 more efficiently.

Thus, the present example provides the particulate matter detection element which is capable of reducing burying of the detection electrodes by the residue of the particulate matter, and capable of preventing reduction of detection sensitivity.

Incidentally, the embodiment 1 shows an example where the main particulate matter included in the exhaust gases is positively charged. In addition, embodiment 1 shows an example where in a target accumulating part, a thickness of a negative electrode of each of the detection electrodes in a laminating direction of the direction electrodes is larger than a thickness of a positive electrode of the detection electrode in the laminating direction. When the main particulate matter included in the exhaust gases is negatively charged, in the target accumulating part, the thickness of the positive electrode in the laminating direction may be larger than the thickness of the negative electrode in the laminating direction.

(Confirmation Test)

In the present test, an influence of the detection sensitivity was confirmed when a ratio W1/W2, which is the thickness W1 of the negative electrode 22 for the thickness W2 of the positive electrode 21 of the particulate matter detection element 1, was changed.

In the present test, the same basic components as for the above-described particulate matter detection element 1 shown in the embodiment 1 were used. A comparison of the detection sensitivity was performed changing the ratio W1/W2, which is the thickness W1 of the negative electrode 22 relative to the thickness W2 of the positive electrode 21. Specifically, five types of particulate matter detection elements of which ratios W1/W2 are respectively set to be 1.0, 1.2, 1.5, 2.7 and 5.0 were used. The thickness W2 of the positive electrode 21 was set to be 4 μm. In addition, an interval of the adjacent detection electrodes 2 in the laminating direction X was set to be 20 μm. In addition, the voltage applied between the positive electrode 21 and the negative electrode 22 was set to be 35 V. Incidentally, the same reference signs as in the embodiment 1 were used for reference signs used in the present example, and drawings according to the present example show the same component elements or the like as in the embodiment 1.

Exhaust gases having a particulate matter concentration of 3 mg/m$^3$ were passed through the exhaust pipe disposed with the particulate matter detection element, at a flow rate of 24 m/s. In addition, an exhaust gas temperature in a vicinity of the particulate matter detection element was 220° C. Under these conditions, a durability test repeating a collection and a regeneration treatment of the particulate matter of 12 min. as one cycle was performed. That is, in the first 10 min. of one cycle, collection of the particulate matter was performed. After this, the regeneration treatment was performed for 2 min. The regeneration treatment was performed by combusting the particulate matter due to heating by a heater.

In addition, after the prescribed cycle of the durability test, change of the detection sensitivity of the particulate matter detection element was examined. The detection sensitivity was determined using a dead mass of the particulate matter detection element. The dead mass means an amount of the particulate matter included in the exhaust gases passing through the exhaust pipe until a conducting path is formed and electric characteristics of the particulate matter detection element are changed in an interval of each cycle. The conducting path is formed on the particulate matter detection element by an accumulation of the particulate matter.

In the particulate matter detection element, a cycle corresponding to vehicle driving 100,000 km is referred to as a 100,000 km corresponding cycle for convenience. In addition, a cycle corresponding to vehicle driving 300,000 km is referred to as a 300,000 km corresponding cycle for convenience. The dead mass of each of five types of particulate matter detection elements was determined in the 100,000 km corresponding cycle. In addition, the dead mass of each of five types of particulate matter detection elements was determined in the 300,000 km corresponding cycle. Each of the dead mass ratios was determined. Measurement results are shown in Table. 1. Incidentally, the dead mass ratio is the ratio of the dead mass measured during the first cycle to the dead mass measured during the predetermined number of cycles.

TABLE 1

| W1/W2 | Equivalent to driving 100,000 km | Equivalent to driving 300,000 km |
|---|---|---|
| 1.0 | 2.4 | No data |
| 1.2 | 1.6 | No data |
| 1.5 | 1.0 | 3.2 |
| 2.7 | 1.0 | 1.0 |
| 5.0 | 1.0 | 1.0 |

The dead mass ratio determined in the 100,000 km corresponding cycle is shown in a column of "Equivalent to driving 100,000 km" in Table. 1. In addition, the dead mass ratio determined in the 300,000 km corresponding cycle is shown in a column of "Equivalent to driving 300,000 km" in Table. 1.

As shown in Table. 1, when the ratio W1/W2 was 1.0 (W1=W2), the dead mass ratio in the 100,000 km corresponding cycle was 2.4 and was large. In contrast, when the thickness W1 of the negative electrode 22 was larger than the thickness W2 of the positive electrode 21, the dead mass ratio was reduced.

In addition, when the ratio W1/W2 was 1.5 or more, no reduction of the detection sensitivity of the particulate matter detection element 1 in the 100,000 km corresponding cycle could be confirmed. Furthermore, when the ratio W1/W2 was 2.7 or more, no reduction of the detection sensitivity of the particulate matter detection element 1 in the 300,000 km corresponding cycle might be also confirmed.

From the above results, in the target accumulating part 5, when the thickness W1 is larger than the thickness W2, durability of the detection sensitivity of the particulate matter detection element may be increased. The thickness W1 is a thickness in the laminating direction X of the detection electrode 2 having the first polarity. The thickness W2 is a thickness in the laminating direction X of the detection electrode 2 having the second polarity. In addition, in the target accumulating part 5, when the thickness W1 is 1.5 or more times the thickness W2, the particulate matter detection element 1, of which the detection sensitivity is highly stable, is obtained. Furthermore, in the target accumulating part 5, it is more preferably that the thickness W1 is 2.7 or more times larger than the thickness W2.

Incidentally, in the particulate matter detection elements having the ratios W1/W2, which are respectively set to be 1.0 and 1.2, the particulate matter might not be determine before completing the 300,000 km corresponding cycle from the start of the durability test. This is considered to be due to the detection electrode being buried in the residue of the particulate matter in an interval before completing the end of the 300,000 km corresponding cycle from the start of the durability test.

REFERENCE SIGNS LIST

1: particulate matter detection element
2: detection electrode
3: insulating member
4: laminated part
5: target accumulating part W1: thickness of detection electrode (negative electrode)
W2: thickness of detection electrode (positive electrode)
X: laminating direction

The invention claimed is:

1. A particulate matter detection element for detecting a particulate matter contained in an exhaust gas discharged from an internal combustion engine comprising:
   a plurality of insulating members made of a material having electrical insulation properties;
   at least one first detection electrode that is laminated on the insulating member and has a first polarity, at least a part thereof is formed into a detection surface so as to expose in a direction orthogonal to a stacking direction to allow deposition of the particulate matter, the first detection electrode of which the detection surface has a first thickness in the stacking direction; and
   at least one second detection electrode that has a second polarity different from that of the first detection electrode and is laminate on the insulating member so as to be adjacent to the first detection electrode with the insulating member interposed therebetween, at least a part thereof is formed into a detection surface so as to expose in a direction orthogonal to a stacking direction to allow deposition of the particulate matter, the second detection electrode of which the detection surface has a second thickness smaller than the first thickness in the stacking direction.

2. The particulate matter detection element of claim 1, wherein the first thickness is 1.5 or more times the second thickness.

* * * * *